United States Patent
Thuering et al.

(10) Patent No.: US 9,482,571 B2
(45) Date of Patent: Nov. 1, 2016

(54) DEVICE FOR MEASURING A FUEL FLOW AND CALIBRATING DEVICE THEREFOR

(75) Inventors: Rainer Thuering, Wiesbaden (DE); Guenter Hagemann, Gifhorn (DE)

(73) Assignee: Horiba Europe GmbH, Darmstadt (DE)

( * ) Notice: Subject to any disclaimer, the term of this patent is extended or adjusted under 35 U.S.C. 154(b) by 446 days.

(21) Appl. No.: 14/114,391

(22) PCT Filed: Mar. 15, 2012

(86) PCT No.: PCT/EP2012/001163
§ 371 (c)(1),
(2), (4) Date: Jan. 20, 2014

(87) PCT Pub. No.: WO2012/146336
PCT Pub. Date: Nov. 1, 2012

(65) Prior Publication Data
US 2014/0216126 A1    Aug. 7, 2014

(30) Foreign Application Priority Data
Apr. 29, 2011    (DE) .......................... 10 2011 100 029

(51) Int. Cl.
| | |
|---|---|
| G01F 25/00 | (2006.01) |
| G01N 9/00 | (2006.01) |
| G01N 11/08 | (2006.01) |
| G01F 9/00 | (2006.01) |
| G01N 11/00 | (2006.01) |

(52) U.S. Cl.
CPC ........... *G01F 25/0038* (2013.01); *G01F 9/005* (2013.01); *G01F 25/003* (2013.01); *G01F 25/0007* (2013.01); *G01N 9/00* (2013.01); *G01N 11/08* (2013.01); *G01N 2011/0006* (2013.01)

(58) Field of Classification Search
CPC .. G01F 9/005; G01F 25/0007; G01F 25/003; G01F 25/0038
See application file for complete search history.

(56) References Cited

U.S. PATENT DOCUMENTS

| | | | |
|---|---|---|---|
| 4,829,831 A | 5/1989 | Kefer et al. | |
| 5,708,201 A * | 1/1998 | Kaub | .................... F02D 33/003 340/439 |
| 2004/0261492 A1 | 12/2004 | Zarkar et al. | |
| 2005/0279867 A1* | 12/2005 | Ismailov | ................. F02D 41/20 239/585.1 |

FOREIGN PATENT DOCUMENTS

| | | |
|---|---|---|
| AT | 6303 U2 | 7/2003 |
| DE | 102006027780 A1 | 12/2007 |
| EP | 1091197 A2 | 4/2001 |
| EP | 1944502 A1 | 7/2008 |
| FR | 2917162 A1 | 12/2008 |

(Continued)

*Primary Examiner* — Paul West
(74) *Attorney, Agent, or Firm* — Murphy, Bilak & Homiller, PLLC (57) ABSTRACT

A device for measuring a fuel flow in a test stand comprises a measuring module (10) for measuring a fuel flow guided through the measuring module (10) as well as a conditioning module (11) arranged downstream of the measuring module (10) for conditioning the fuel. Moreover, a verification module (19) is provided downstream of the measuring module (10) for checking the measuring precision of the measuring module (10). The fuel may be guided optionally to the conditioning module (11) or to the verification module (19). The verification module (19) is an integral part of the device may have an injector (26) as a dosing unit for extracting an exactly defined reference fuel quantity.

19 Claims, 4 Drawing Sheets (56) References Cited

FOREIGN PATENT DOCUMENTS

| JP | 54117177 U | 1/1978 |
| JP | 6352015 A | 3/1988 |
| JP | 11101153 A | 4/1999 |
| JP | 2004288189 A | 10/2004 |
| JP | 2006012872 A | 1/2006 |
| JP | 2006337346 A | 12/2006 |
| WO | 0233361 A2 | 4/2002 |
| WO | 2008095836 A2 | 8/2008 |

\* cited by examiner

DEVICE FOR MEASURING A FUEL FLOW AND CALIBRATING DEVICE THEREFOR

The invention regards a device for measuring a fuel flow according to the preamble of claim 1.

Such a fuel flow rate measuring device can be used in particular at a test stand for combustion motors. The test stand is for example used in motor development for recording the performance of motors to be tested. Beside the pollutant emission the fuel consumption of a combustion motor is an essential parameter, which should be recorded as precisely as possible during the test procedure.

In order to evaluate the motor power, it is necessary to determine the amount of combusted fuel and the energy density of the combusted fuel as precise as possible. To this end fuel flow rate measuring devices have been developed which supply a combustion motor used as testee with fuel, wherein the parameters of the fuel (fuel temperature, fuel pressure etc.) are kept constant. In parallel to providing the fuel conditioned in this way the mass flow of the fuel is recorded, in order to be able to determine the consumption of the motor.

During operation of the test stand or the fuel flow rate gauger the measuring quality of the fuel flow rate measuring device has to be ensured. These requirements result not only from technical considerations, but also from various quality provisions (ISO 9000; VDA Guidelines 6.1 and 6.4; GUM—Guide to the Determination of Uncertainties in Measurements). Accordingly, regular calibrations of the flow rate measuring devices are necessary, which are very involved in practice, and which can often only be conducted by specialists. Typical calibration laboratories are normally not able to calibrate a fuel flow rate gauger of a test stand, as the know-how necessary thereto is missing. The technical rules and standards demand in particular a traceability of the calibration procedures such that the calibration arrangements are completely documented also retrospectively.

Different devices and methods are known in the state of the art which can be used for calibrating a fuel flow rate measuring device.

From EP 1 091 197 A1 a device for continuous measurement of dynamic fuel consumption of a combustion motor is known, which provides downstream of a pump in a fuel supply pipe a continuously measuring mass flow sensor. By using a discontinuously measuring calibration unit the mass flow sensor can be calibrated, wherein the calibration unit determines during a calibration the fuel consumption measured also by the mass flow sensor. During the calibration all test stand and system relevant influencing quantities are taken into account in the measurement result as a sum, without the possibility to evaluate single parameters separated from each other. The actually aimed at calibration of the mass flow sensor is therefore only restrictedly possible, in particular for small flow rates.

In this manner in presently used calibration methods for the most part all measurement imprecisions are recorded together. For this purpose so-called calibration carts, i.e. carts on which calibration devices are installed, are rolled into the test stands and installed therein into the fuel conduction upstream or downstream of the fuel flow rate measuring device. To this end the fuel pipes have to be opened such that fuel can leak out, which may lead to a danger for persons in the surrounding of the test stand. Moreover, the operation of the test stand has to be interrupted for a longer period of time in order to install the calibration cart. The calibration method itself has to be executed by accordingly qualified operators, which are however not employed at the location of the test stand, but are provided from the manufacturer of the fuel flow rate measuring device to be calibrated. The availability of these persons is therefore limited and requires an accurate time scheduling.

Figure 7:
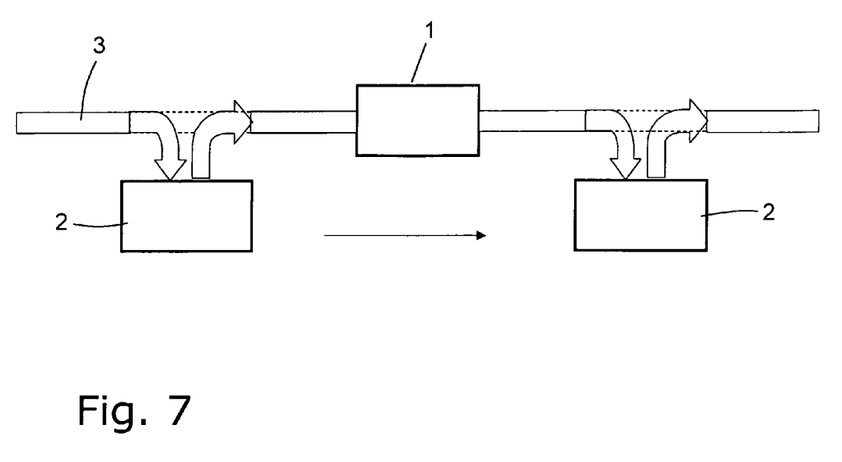
FIG. 7 a fuel flow rate measuring device according to the state of the art.

FIG. 7 shows the structure of a known fuel flow rate measuring device 1 with a reference device 2, which may be arranged upstream or downstream of the fuel flow rate measuring device 1 in a fuel pipe 3. The reference device 2 is arranged on a cart and is movable such that it can be moved on demand to the test stand which should be calibrated. In order to install the reference device 2 the fuel pipe 3 has to be opened such that the reference device 2 can be integrated.

The invention solves the problem to give a device for measuring a fuel flow which can be calibrated reliably and according to national and international standards without making an important interruption of operation necessary. Moreover, it is desirable that the calibration arrangements can be performed by operators which are not particularly schooled for calibrating such devices.

The problem is solved by a device according to claim 1. Further developments of the invention as well as advantageous methods using the present device are given in the dependent claims.

A device for measuring a fuel flow comprises: a measuring module for measuring the fuel flow guided through the measuring module, a downstream of the measuring module arranged conditioning module for conditioning the fuel and a verification module provided downstream of the measuring module for checking the measuring precision of the measuring module. The verification module is firmly and permanently installed as an integral part of the device and connected via a pipe or line with the measuring module such that fuel can be guided downstream of the measuring module to the verification module.

The device serves in particular for measuring the fuel flow to a combustion motor of a test stand. The measuring module performs the actual function of measuring during operation of the device, namely in particular during supplying a testee with fuel. The conditioning module serves to provide the fuel in a desired quality, in particular with regard to pressure and temperature. A constant temperature and a constant pressure are basic conditions for a precise measuring of the actual fuel consumption of a combustion motor.

The verification module is integrated in the device and therefore a fixed part of the device. The verification module serves to verify the values for the fuel flow measured by the measuring module. Insofar the verification module may also be used for calibrating the measuring module.

Since the verification module is integrated into the measuring device, the involved reconstruction of the measuring device for purposes of calibration is dispensable, which occasionally endangers also the acting persons. Rather, it is possible to automatize the calibration procedure by using the verification module such that the procedure may also be carried out automatically by untrained workers. As a result it is for example sufficient to show the operator of the measuring device merely an "Ok" sign from which the operator can deduce that the fuel flow rate measuring device is usable and provides the necessary measuring quality.

The measuring quality or—conversely—the measurement uncertainty may be influenced by numerous parameters. As will be shown later it is possible to provide respective units in the verification module which address these thoughts and which may determine the precision according to single influence parameters. Influence parameters are for example the surrounding conditions, the conditions of the fuel pipe or line, the temperature of the fuel as well as the temperature regulation, the fuel pressure and the fuel pressure regulation, the quality of calibration, the stability of calibration as well as statistical influence parameters (standard deviation). The verification module takes this into account and is able to justify at least single pieces of the overall measurement uncertainty of the fuel consumption and to deduce thereof the exact determination of the total measurement uncertainty of the fuel flow rate gauger. In this way the sensors incorporated in the measuring module can be checked individually with regard to their measuring precision or the calibration state.

According to this the verification module may be formed for checking at least one parameter which effects the measuring precision of the measuring module. The corresponding parameters result for example from the standard work GUM (Guide to the Determination of Uncertainties in Measurements), a standard work based on international agreements.

The fuel quantity extracted with the verification module is compared with the fuel quantity of the flow rate measuring device in the measuring module, in order to check the precision of the measurement values of the flow rate measuring device and hence to check its calibration state.

Between the measuring module and the conditioning module a main pipe or line may be provided for guiding the fuel from the measuring module to the conditioning module, wherein a secondary pipe or line to the verification module may be provided branching off from the main pipe at a branching point.

By means of the branching point it is possible to guide the fuel downstream of the measuring module optionally to the conditioning module or to the verification module. In normal testing operation the fuel should be guided from the measuring module over the conditioning module to the combustion motor connectable to the conditioning module. On the other hand during calibration or verification operation the fuel should exclusively be guided downstream of the measuring module to the verification module.

To this end a closing valve unit may be provided between the part of the main pipe running between the branching point and the conditioning module. By using the closing valve unit a fuel flow to the conditioning module may be interrupted on demand.

Just as well a closing valve unit may be provided in the part of the secondary line running between the branching point and the verification module. This closing valve unit may be closed in normal test operation, when no fuel has to be guided to the verification module.

Concerning the dimensioning of the pipes or lines it is desirable that the line paths are as short as possible, in order to minimize the volume of the pipes between the measuring module and the verification module. Moreover, the pipes should be isolated, in order to be able to exclude temperature influences.

In the measuring module a preconditioning unit and downstream of the preconditioning unit a flow rate measuring unit for measuring the fuel flow flowing through the measuring module as a measurement fuel quantity may be provided. The preconditioning unit serves for conditioning the fuel supplied from a storing tank (fuel tank) for example by a fuel pump at this stage with respect to pressure and temperature such that the downstream flow rate measuring unit receives the fuel in the desired manner. It is appropriate that the properties to which the fuel is set by the preconditioning unit are identical to the properties to be set by the conditioning module.

According to one embodiment the verification module may comprise a dosing module for extracting an exactly defined quantity of fuel serving as a reference fuel quantity. In this process the fuel quantity determined by the measuring module and the reference fuel quantity determined by the dosing unit may be compared, in order to determine a measuring precision of the measuring module.

The dosing unit is hence able to extract a defined fuel quantity with special precision, namely the reference fuel quantity. If the measuring module has the necessary measuring precision the measuring module will therefore measure exactly the same fuel quantity (measurement fuel quantity), as the fuel quantity flows because of the same pressure and temperature conditions in the whole system also through the measuring module located upstream. By comparison between the measurement fuel quantity determined by the measuring module and the reference measuring quantity it may be evaluated whether the measuring module achieves the necessary measuring precision or whether an adjustment of the measuring module is necessary.

The dosing unit may be a fuel injector unit. A fuel injector unit is particularly suited to dose the reference fuel quantity according to the requirements with high precision.

An injector unit or a fuel injector has been proven as reliable fuel dosing unit for combustion motors in practice. With the injector different well-defined flow rates can be realized reproducible. Therefore, by using the injector the fuel quantity necessary for the comparison considerations in the verification module may be extracted from the connecting pipe between the measuring module and the conditioning module. Such an injector is known for example from DE 10 2006 027 780 A1.

In a variant the verification module has besides the dosing unit a first pressure sensor arranged upstream of the dosing unit for determining the pressure of the fuel upstream of the dosing unit as well as a second pressure sensor arranged downstream of the dosing unit for determining the pressure of the fuel downstream of the dosing unit. Still a temperature sensor for determining the temperature of the fuel upstream or downstream of the dosing unit may be provided.

Hence, besides the dosing unit only three further sensors are necessary as measurement devices in the verification module in the variant. All other information is known because of the following relation.

As already discussed above, the dosing unit may be realized advantageously in form of a fuel injector. The fuel quantity m forwarded by the injector depends on five influence parameters such that results $$m = f(\Delta p, t, \rho, \ddot{o}_t, k),$$

with:
m=the fuel quantity forwarded by the injector
$\Delta p$=pressure difference before and behind the injector
t=temperature of the fuel
$\rho$=viscosity of the fuel (information of the manufacturer)
$\ddot{o}_t$=opening time of the injector
k=characteristic diagram of the injector (defined by the manufacturer).

In the variant described above the pressure difference may be measured via the dosing unit or via the injector as well as the temperature of the fuel may be measured. The viscosity of the fuel is a characteristic parameter which is guaranteed by the fuel manufacturer and therefore known. The opening and closing behavior of the injector is defined by the injector characteristic diagram of the manufacturer and results from the first calibration of the injector. A measuring method for determining the injector characteristic diagram is by the way also described in EP 1 944 502 A1.

Together with the measurement parameters indicated here (temperature and pressure difference) and the characteristic features of the injector and the fuel the fuel quantity m flowing through the injector can be set with high precision by the opening time $ö_t$ of the injector valve. The injector is therefore excellently suited for forwarding the reference fuel quantity.

In a variant the verification module may have a flow rate standard serving as a reference flow rate measuring unit for measuring the reference fuel quantity extracted by the dosing unit as a so-called calibration fuel quantity. In this process reference fuel quantity extracted by the dosing unit and the calibration fuel quantity measured by the reference flow rate measuring unit may be compared, in order to determine the dosing precision of the dosing unit.

In this variant the verification module gets extended by a flow rate standard or reference standard in form of the reference flow rate measuring unit such that the whole flow rate of the reference volume flows through the integrated flow rate measuring unit in the measuring module as well as through the reference flow rate measuring unit. In this way the volume flow rate measured by the measuring module may be directly compared to the value measured by the reference flow rate measuring unit. This allows for a traceable calibration. In particular, the precision of the dosing unit may be checked in this manner, as the reference fuel quantity predetermined by the dosing unit by the extraction gets recorded in equal measure by the flow rate measuring unit in the measuring module and by the reference flow rate measuring unit in the verification module. Then, the components may be verified with respect to each other.

In another variant the measuring module may have a density measuring unit for determining the density of the fuel flowing through the measuring module. The verification module may have a density standard serving as a reference density measuring unit for determining a density of the fuel flowing through the verification module serving as a reference density. In this process the measurement density determined by the density measuring unit of the measuring module and the reference density determined by the reference density measuring unit may be compared, in order to determine a measuring precision of the measuring module.

In this variant the density measured by the density measuring unit integrated in the measuring module (measurement density) may be compared directly to the density value measured by the reference density measuring unit. Again, this allows for a traceable calibration of the density measuring unit and hence of the mass flow rate.

In a further variant the dosing unit, for example an injector, has a characteristic diagram. The verification module may have additionally at least one of the following sensors: a pressure difference sensor or also more than one, e.g. two pressure difference sensors for determining a pressure difference between an inlet and an outlet of the dosing unit, a fuel temperature sensor for determining the fuel temperature upstream of the dosing unit, and/or a voltage or current sensor for determining an electrical voltage or a current for activating the dosing unit. Because of measurement results of at least one of these sensors the characteristic diagram of the dosing unit may be corrected.

The mentioned sensors serve as reference sensors and are used in this variant as so-called transfer standards (seal of quality), which are calibrated and monitored as measure and testing means by accredited calibration laboratories. Thus, the traceability to national standards as demanded by established quality management systems is ensured.

In a further variant a further verification module may be provided downstream of the conditioning module for simulating a combustion motor typically connectable to the conditioning module downstream of the conditioning module. The further verification module may be formed for extracting differing fuel quantities according to the usual variable consumption of fuel by a combustion motor.

This variant may be helpful for determining whether a deviation in measurement results, which is not explicable at first sight, is caused by the combustion motor or by the measuring environment. In order to determine the plausibility of the fuel consumption of the combustion motor the combustion motor is separated from the measuring device and replaced by the further verification module. The further verification module simulates differing consumption states analogous to the usual consumption of a combustion motor. According to this a fuel injector may be provided again in the further verification module, which corresponds to the injector of a combustion motor. The fuel flowing through the injector simulates the fuel consumed by the combustion motor.

In the measuring device a controlling and evaluation unit may be provided for performing of at least a part of the following functions: controlling of the components of the device, operating the measuring units and sensors, controlling the closing valve units, activating of the verification module, recording of measurement values, evaluating and comparing of the measurement value.

The controlling and evaluation unit may for example be realized by means of a computer controlling program, which may be a component of the controls of the fuel flow rate gauger. The computer controlling program carries out the checking of the calibration status by controlling the verification module and needs for example only be activated by an operator of the test stand for example by pressing a key. During the verification or calibration procedure no further measures have to be conducted by the operator.

In one embodiment a method for checking a calibration status of one of the aforementioned fuel flow rate measuring devices is indicated. The method comprises the steps of:
  extracting an exactly defined reference fuel quantity from the main pipe or line between the measuring module and the conditioning module;
  determining a fuel quantity flowing through the measuring module necessary for providing the reference fuel quantity as measured fuel quantity by the measuring module;
  comparing the reference fuel quantity to the measurement fuel quantity and determining a precision of the measurement values generated by the measuring module based on a deviation between the measurement fuel quantity and the reference fuel quantity.

Further, a method for determining a fuel type used in a test stand is indicated. In one and the same test stand typically different motor types are tested which each need a suitable fuel type. The verification module described above may also be used to determine the fuel type automatically, which is comprised in the fuel pipes or lines to the motor. A test stand automatization system may be use this functionality in order to check whether the motor located on the test stand is supplied with the required fuel type, i.e. whether the "right" fuel type, for example diesel, gasoline/petrol or ethanol, is supplied to the fuel pipes.

The fuel flow rate measuring device is interconnected into the fuel pipe or line between the fuel reservoir tank and the motor to be tested. At first the fuel pipes to the combustion motor are rinsed with the new fuel. Then, the branching point to the verification module gets rinsed. During this rinsing the injector of the verification module has to forward at least as much fuel as is included in the secondary pipe or line.

After the rinsing the fuel type may be determined by means of the method described in the following.

According to this a method for determining a fuel type by means of the device described above is indicated with the steps of
determining a fuel quantity forwarded by the dosing unit;
determining a pressure difference between an inlet and an outlet of the dosing unit;
determining the temperature of the fuel;
determining an opening time of the dosing unit;
providing a characteristic diagram of the dosing unit;
deducing a viscosity of the fuel based on the fuel quantity, the pressure difference, the temperature, the opening time and the characteristic diagram;
determining the fuel type based on the viscosity.

The parameters correspond to the relation explained already above $m=f(\Delta p, t, \rho, ö_t, k)$. This relation can also be reordered to $$\rho = f(\Delta p, t, m, ö_t, k).$$

Hence, the viscosity $\rho$ depends from the other quantities which however are all known.

In particular, the method is carried out by the following steps: dosing a well-defined fuel quantity by the injector; determining the viscosity of the "unknown" fuel by means of the above equation; determining the fuel type by classification by means of known viscosity information. For example diesel has a viscosity of 2 . . . 4.5 mm$^2$/s, Euro Super 95 a viscosity of approx. 0.53 mm$^2$/s and ethanol the viscosity of approx. 1.2 mm$^2$/s. Because of these viscosities differing significantly the type of any present fuel may be deduced.

Figure 1:
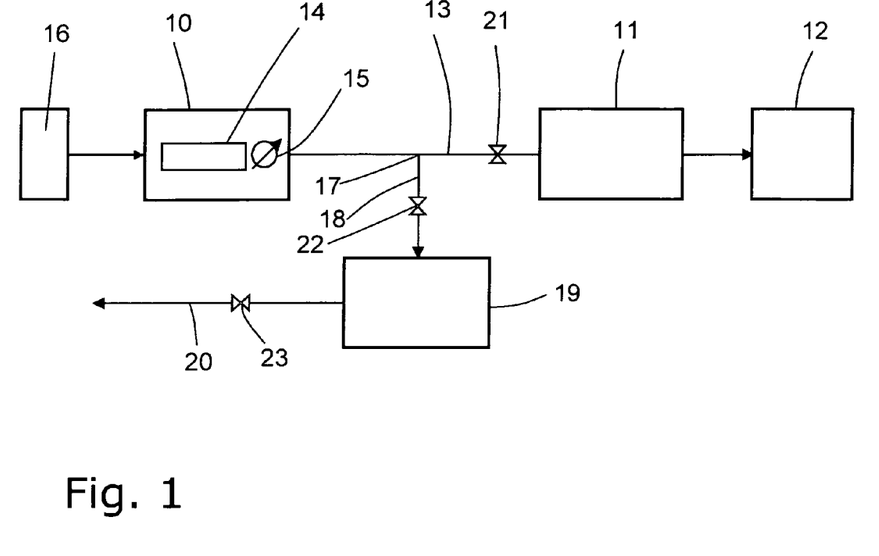
FIG. 1 the structure of a device for measuring a fuel flow rate in a schematic illustration.

These and further advantages and features of the invention are discussed in the following with regard to examples and by means of the accompanying figures. It shows:

FIG. 1 shows in principle the structure of a device according to the invention for measuring a fuel flow rate (fuel flow rate measuring device).

The device has a measuring module 10 as well as a conditioning module 11 to which a combustion motor 12 is connectable which does not belong to the device. The measuring module 10 is connected via a main pipe or line 13 with the conditioning module 11.

In the measuring module 10 a preconditioning unit 14 as well as a flow rate measuring unit 15 are provided. The measuring module 10 serves for measuring the fuel flow rate guided through the measuring module 10. For example, the fuel may be extracted from a fuel reservoir tank 16 which does not belong to the device.

The preconditioning unit 14 in the measuring module 10 serves for setting the supplied fuel to a specific temperature and a specific pressure. Subsequently, the fuel flows through the flow rate measuring unit and gets via the main pipe 13 to the conditioning module 11 where a temperature and pressure of the fuel gets conditioned anew, before the fuel is supplied to the combustion motor 12. The components are constituent parts of a test stand in which the performance of the combustion motor 12 is to be tested.

In the main pipe or line 13 a branching point 17 is provided at which a secondary pipe or line 18 branches off from the main pipe 13 and leads to a verification module 19. The fuel flowing through the verification module 19 is consecutively discharged over a discharge 20, for example again to the fuel reservoir tank 16.

In the main pipe 13 between the branching point 17 and the conditioning module 11 a first closing valve 21 is arranged. Furthermore, a second closing valve 22 is provided in the secondary pipe 18 and a third closing valve 23 is provided in the discharge 20. By means of the closing valves 21, 22, and 23 the fuel flow downstream of the measuring module may be guided selectively only to the conditioning module 11 or only to the verification module 19.

The verification module 19 is an integral part of the device and is connected firmly with the measuring module 11 via the pipes 13, 18, which are as short as possible and heat isolated if necessary. Hence, the verification module 19 is present permanently such that the calibration or verification procedures performed by the verification module can be performed at any time. It is—in distinction of the prior art according to FIG. 7—not necessary to open a fuel line (for example the main pipe 13) if necessary and to integrate a respective verification module.

Figure 2:
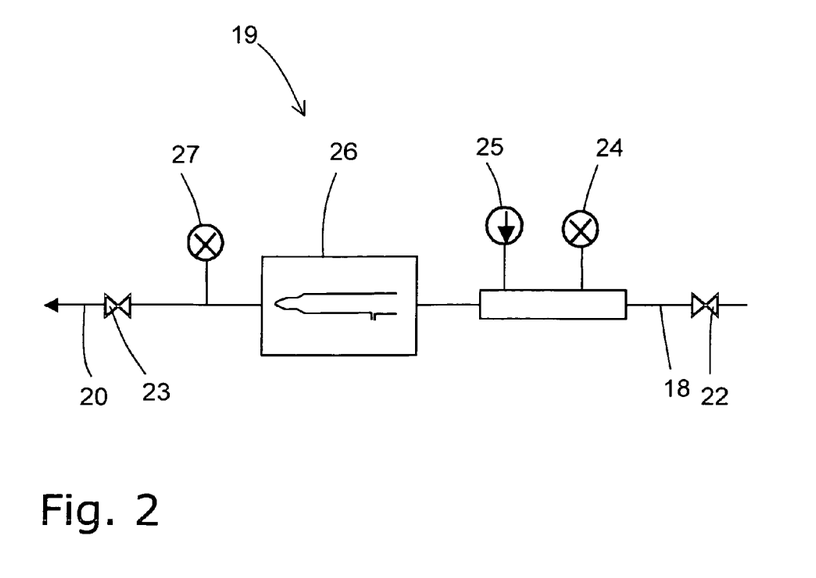
FIG. 2 the structure of a verification module, which is used in the device of FIG. 1, in a schematic illustration.

The structure of an example of a verification module is shown in FIG. 2.

Downstream from the second closing valve 22 and the secondary pipe 18 a first pressure sensor 24 and a temperature sensor 25 are provided which are followed downstream by an injector 26 serving as a dosing unit. Downstream from the injector 26 a second pressure sensor 27 is provided.

The injector, for example a fuel injector of a motor vehicle as known from DE 10 2006 027 780, was discussed already above. It serves for example for injecting of fuel into the cylinder of a combustion motor and is especially well suited for precisely forwarding a reference fuel quantity and hence to extract the fuel quantity from the main pipe 13 running upstream of the secondary pipe 18.

In the ideal case the reference fuel quantity forwarded by the injector 26 corresponds to the quantity which is at the same time determined by the flow rate measuring unit 15 in the measuring module 10. In case of a deviation of the values the flow rate measuring unit 15 may be readjusted such that a calibration of the measuring module is possible in this manner.

Before the calibration starts, the first closing valve 21 to the conditioning module 11 has to be closed. The two closing valves 22 and 23 have be to opened such that the fuel is forwarded exclusively through the measuring module 10 and the verification module 19.

After ending the verification procedure both closing valves 22, 23 may be closed again and the first closing valve 21 may be opened such that afterwards the combustion motor 12 can be tested in the test stand. The calibrated flow rate measuring unit 15 should then be able to determine with high precision the fuel flow rate which is required by the combustion motor 12.

Figure 3:
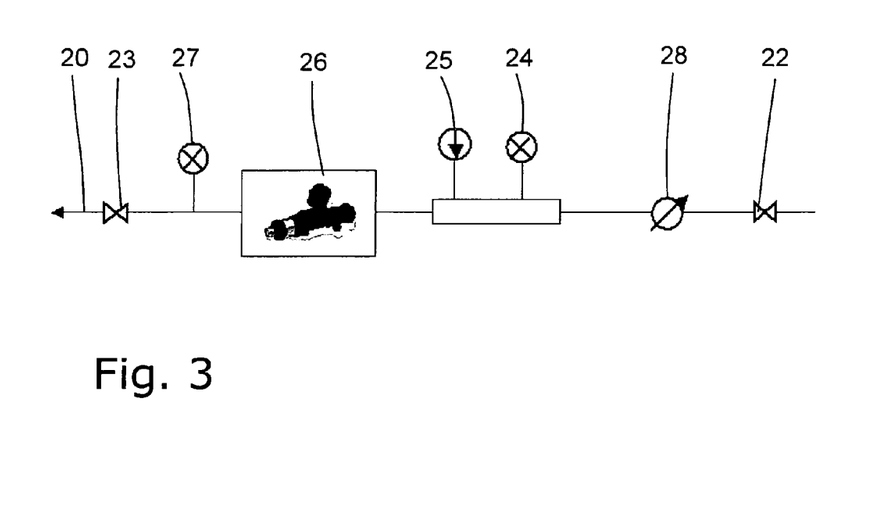
FIG. 3 another embodiment of the verification module.

FIG. 3 shows a variant of the verification module of FIG. 2.

In addition to the components indicated already above a reference flow rate measuring unit 28 serving as a flow rate standard is provided upstream of the injector 26. The reference flow rate measuring unit 28 is a highly precise measuring instrument, calibrated for example in a laboratory, and is thus able to measure the flowing fuel with highest precision.

By means of the reference flow rate measuring unit 28 it is on the one hand possible to check also the flow rate measuring unit 15 directly by comparing both measurement values with each other. In addition, it is also possible to calibrate the injector 26 by means of the reference flow rate measuring unit 28. The injector 26 is operated according to indications of the manufacturer and the characteristic diagrams, in order to dose a specific reference fuel quantity. This reference fuel quantity is also recorded by the reference flow rate measuring unit 28 and measured, wherein the measurement result is called "calibration fuel quantity" herein. If the measurement results deviate from each other the injector characteristic diagram of the injector 26 has to be corrected.

Figure 4:
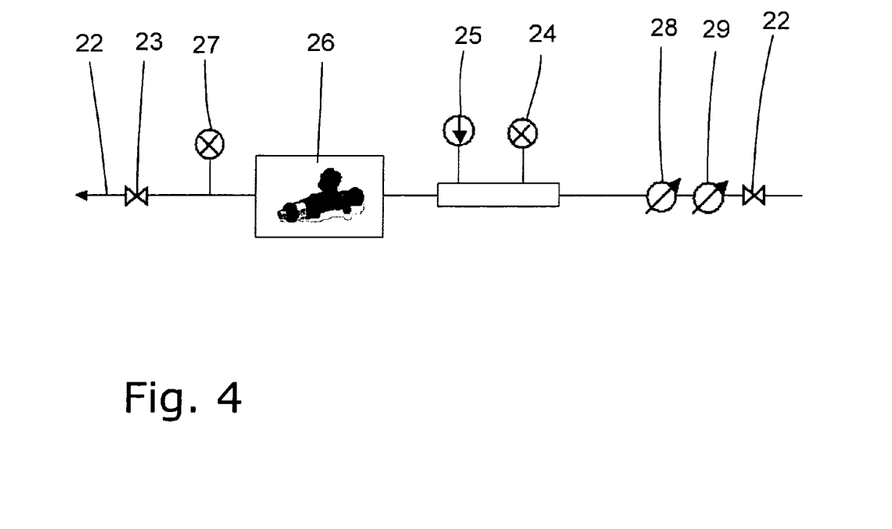
FIG. 4 a development of the verification module.

FIG. 4 shows a further variant of the verification module of FIG. 3. In addition a highly precise reference density measuring unit 29, which is e.g. calibrated in a laboratory, is provided as a density standard. By this means the density measured by the density sensor integrated in the measuring module 10 may be compared directly to the measurement value measured by the reference density measuring unit 29. This allows again for a traceable calibration of the density sensor in the measuring module 10 and hence also of the mass flow rate.

According to the verification modules of FIGS. 2 to 4 it becomes apparent how single parameters of the measuring module 10, which codetermine the overall precision of the measuring module 10, may be calibrated by means of a suitable structure of the verification module 19.

Figure 5:
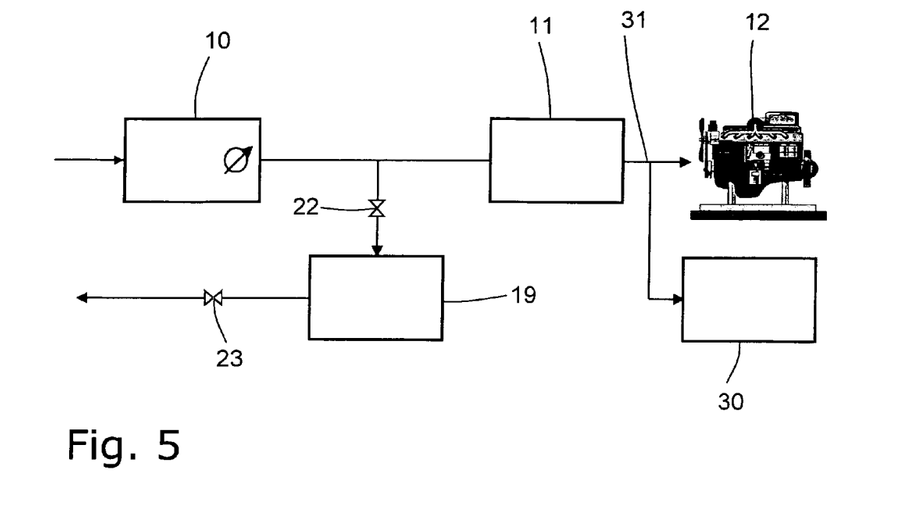
FIG. 5 an embodiment with a further verification module instead of a combustion motor.

FIG. 5 shows a variant in which downstream of the conditioning module 11 and parallel to the combustion motor 12 a further (second) verification module 30 is arranged.

The second verification module 30 may—e.g. via a branching 31—be connected to the conditioning module 11 as an alternative to the combustion motor 12 and may simulate the fuel consumption behaviour of the combustion motor 12. In this manner in case of need it may be tested whether the combustion motor 12 or the whole measuring device shows a plausible behaviour.

Again, also in the second verification module 30 an injector may be provided, which is formed for dosing an exactly defined fuel quantity.

Figure 6:
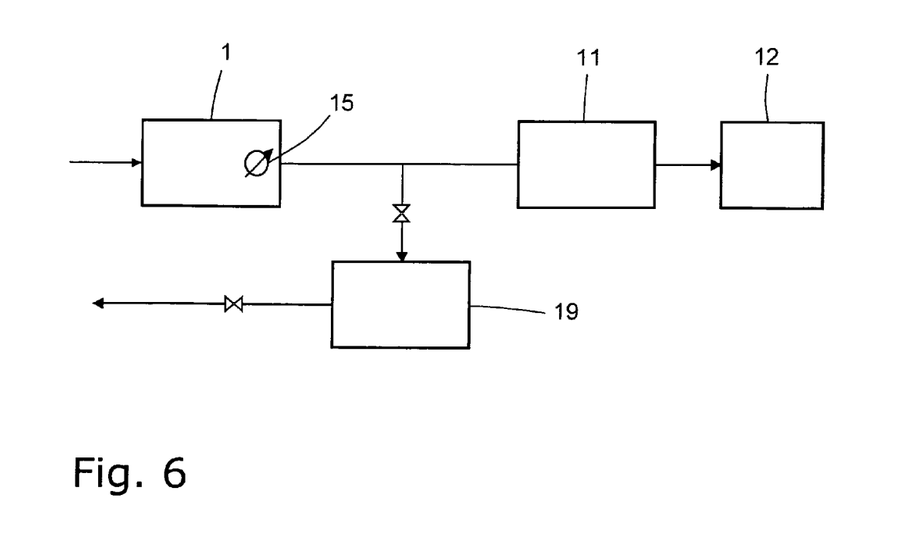
FIG. 6 an arrangement for determining a fuel type.

FIG. 6 shows a variant to the arrangement of FIG. 1.

In this case the verification module is alternatively or additionally formed to determine the fuel type according to the viscosity of the forwarded fuel. The method necessary for this has been discussed already above such that in order to avoid repetitions it is resigned from a discussion at this place.

The invention claimed is:

1. A device for measuring a fuel flow, the device comprising:
    a measuring module operable to measure a fuel flow guided through the measuring module;
    a conditioning module downstream of the measuring module and operable to condition the fuel;
    a verification module downstream of the measuring module and operable to check the measuring precision of the measuring module, the verification module installed firmly and permanently as an integral part of the device and connected with the measuring module such that the fuel can be guided from the measuring module downstream to the verification module;
    a main pipe for guiding the fuel from the measuring module to the conditioning module; and
    a secondary pipe branching off to the verification module from the main pipe at a branching point,
    wherein the verification module has a dosing unit with a fuel injector unit operable to extract an exactly defined quantity of fuel serving as a reference fuel quantity,
    wherein the measurement fuel quantity determined by the measuring module and the reference fuel quantity determined by the dosing unit are comparable in order to determine a measuring precision of the measuring module.

2. The device of claim 1, wherein the verification module is operable to check at least one of the parameters concerning the measuring precision of the measuring module.

3. The device of claim 1, further comprising a closing valve unit disposed in a part of the main pipe running between the branching point and the conditioning module.

4. The device of claim 3, further comprising:
    a controlling and evaluation unit operable to perform at least a part of controlling of the closing valve unit.

5. The device of claim 1, further comprising a closing valve unit disposed in a part of the secondary pipe running between the branching point and the verification module.

6. The device of claim 5, further comprising:
    a controlling and evaluation unit operable to perform at least a part of controlling of the closing valve unit.

7. The device of claim 1, wherein the measuring module comprises a preconditioning unit and downstream of the preconditioning unit a flow rate measuring unit operable to measure the fuel flow flowing through the measuring module as measurement fuel quantity are provided.

8. The device of claim 7, further comprising:
    a controlling and evaluation unit operable to perform at least a part of operating the flow rate measuring unit.

9. The device of claim 1, wherein the verification module comprises:
    a first pressure sensor upstream of the dosing unit and operable to determine the pressure of the fuel upstream of the dosing unit;
    a second pressure sensor downstream of the dosing unit and operable to determine the pressure of the fuel downstream of the dosing unit; and
    a temperature sensor operable to determine the temperature of the fuel.

10. The device of claim 9, further comprising:
    a controlling and evaluation unit operable to perform at least a part of operating the sensors.

11. The device of claim 1, wherein the verification module comprises a reference flow rate measuring unit operable to measure the reference fuel quantity extracted by the dosing unit as calibration fuel quantity, and wherein the reference fuel quantity extracted by the dosing unit and the calibration fuel quantity measured by the reference flow rate measuring unit are comparable in order to determine the dosing precision of the dosing unit.

12. The device of claim 11, further comprising:
a controlling and evaluation unit operable to perform at least a part of operating the reference flow rate measuring unit.

13. The device of claim 1, wherein the measuring module comprises a density measuring unit operable to determine the density of the fuel flow through the measuring module, wherein the verification module comprises a reference density measuring unit operable to determine a density of the fuel flowing through the verification module serving as a reference density, and wherein the density determined by the density measuring unit and the reference density determined by the reference density measuring unit are comparable in order to determine a measuring precision of the measuring module.

14. The device of claim 1, further comprising:
a controlling and evaluation unit operable to perform at least a part of operating the density measuring unit and the reference density measuring unit.

15. The device of claim 1, wherein the dosing unit comprises at least one of the following sensors:
a pressure difference sensor operable to determine a pressure difference between an inlet and an outlet of the dosing unit;
a fuel temperature sensor operable to determine the fuel temperature upstream of the dosing, unit;
a voltage sensor operable to determine an electric voltage necessary for activating the dosing unit; and
a current sensor operable to determine an electrical current necessary for activating the dosing unit,
wherein because of measurement results of at least one of the sensors, a characteristic diagram of the dosing unit is correctable.

16. The device of claim 1, further comprising:
a further verification module provided downstream of the conditioning module and operable to simulate a combustion motor connectable downstream of the conditioning module to the conditioning module, the further verification module operable to extract differing fuel quantities according to variable consumptions of fuel by a combustion motor.

17. The device of claim 1, further comprising:
a controlling and evaluation unit operable to perform at least a part of activating the verification module.

18. A method for checking a calibration status of a device comprising a measuring module operable to measure a fuel flow guided through the measuring module, a conditioning module downstream of the measuring module and operable to condition the fuel, a verification module downstream of the measuring module and operable to check the measuring precision of the measuring module, the verification module installed firmly and permanently as an integral part of the device and connected with the measuring module such that the fuel can be guided from the measuring module downstream to the verification module, a main pipe for guiding the fuel from the measuring module to the conditioning module is disposed between the measuring module and the conditioning module, and a secondary pipe branching off to the verification module from the main pipe at a branching point, wherein the verification module has a dosing unit with a fuel injector unit operable to extract an exactly defined quantity of fuel serving as a reference fuel quantity, wherein the measurement fuel quantity determined by the measuring module and the reference fuel quantity determined by the dosing unit are comparable, in order to determine a measuring precision of the measuring module, the method comprising:
extracting an exactly defined reference fuel quantity from the main pipe between the measuring module and the conditioning module;
measuring, by the measuring module, a fuel quantity flowing through the measuring module, which flow of the fuel quantity is caused when the reference fuel quantity is extracted; and
comparing the reference fuel quantity with the measurement fuel quantity and determining a precision of the measuring values generated by the measuring module based on a deviation between the measuring fuel quantity and the reference fuel quantity.

19. A method for determining a fuel type by a device comprising a measuring module operable to measure a fuel flow guided through the measuring module, a conditioning module downstream of the measuring module and operable to condition the fuel, a verification module downstream of the measuring module and operable to check the measuring precision of the measuring module, the verification module installed firmly and permanently as an integral part of the device and connected with the measuring module such that the fuel can be guided from the measuring module downstream to the verification module, a main pipe for guiding the fuel from the measuring module to the conditioning module is disposed between the measuring module and the conditioning module, and a secondary pipe branching off to the verification module from the main pipe at a branching point, wherein the verification module has a dosing unit with a fuel injector unit operable to extract an exactly defined quantity of fuel serving as a reference fuel quantity, wherein the measurement fuel quantity determined by the measuring module and the reference fuel quantity determined by the dosing unit are comparable, in order to determine a measuring precision of the measuring module, the method comprising:
determining a fuel quantity forwarded by the dosing unit;
determining a pressure difference between an inlet and an outlet of the dosing unit;
determining the temperature of the fuel;
determining an opening time of the dosing unit;
providing a parameter characteristic diagram of the dosing unit;
deducing a viscosity of the fuel based on the fuel quantity, the pressure difference, the temperature, the opening time, and the parameter characteristic diagram; and
determining the fuel type according to the viscosity.

* * * * *